United States Patent
Potyrailo et al.

(10) Patent No.: US 10,261,036 B2
(45) Date of Patent: Apr. 16, 2019

(54) SENSING SYSTEM AND AN ASSOCIATED METHOD THEREOF

(71) Applicant: General Electric Company, Schenectady, NY (US)

(72) Inventors: Radislav Alexandrovich Potyrailo, Niskayuna, NY (US); Steven YueHin Go, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 15/187,934

(22) Filed: Jun. 21, 2016

(65) Prior Publication Data
US 2017/0363555 A1    Dec. 21, 2017

(51) Int. Cl.
*G01N 27/02* (2006.01)
*G01N 33/28* (2006.01)

(52) U.S. Cl.
CPC ....... *G01N 27/026* (2013.01); *G01N 33/2888* (2013.01); *G01N 27/028* (2013.01)

(58) Field of Classification Search
CPC ...... G01N 27/00; G01N 27/02; G01N 27/023; G01N 27/025; G01N 27/026; G01N 27/028; G01N 33/00; G01N 33/26; G01N 33/28; G01N 33/2888
USPC ................................ 324/600, 649, 654, 655
See application file for complete search history.

(56) References Cited

U.S. PATENT DOCUMENTS

| | | | | |
|---|---|---|---|---|
| 3,795,855 A | * | 3/1974 | Browning | G01N 24/08 324/322 |
| 4,255,975 A | * | 3/1981 | Debreuille | E21B 47/00 33/313 |
| 5,268,642 A | * | 12/1993 | Uchidomi | G01R 27/22 250/551 |
| 5,614,830 A | | 3/1997 | Dickert et al. | |
| 7,911,345 B2 | | 3/2011 | Potyrailo et al. | |
| 7,928,741 B2 | | 4/2011 | Hedges et al. | |
| 8,155,891 B2 | | 4/2012 | Kong et al. | |
| 8,186,345 B2 | * | 5/2012 | Payton | A61M 16/1075 128/204.17 |
| 8,318,099 B2 | | 11/2012 | Potyrailo et al. | |

(Continued)

FOREIGN PATENT DOCUMENTS

| | | |
|---|---|---|
| WO | 2006066714 A1 | 6/2006 |
| WO | 2011/053234 A1 | 5/2011 |
| WO | 2015180891 A1 | 12/2015 |

OTHER PUBLICATIONS

International Search Report and Written Opinion issued in connection with corresponding PCT Application No. PCT/US2017/036120 dated Aug. 25, 2017.

(Continued)

*Primary Examiner* — Hoai-An D. Nguyen
(74) *Attorney, Agent, or Firm* — Ernest G. Cusick (57) ABSTRACT

A sensing system for monitoring an industrial fluid is presented. The sensing system includes a housing and a sensor probe disposed at least partially in the housing, where the sensor probe includes a substrate, a sensing region disposed on the substrate, a first coil disposed on the substrate and coupled to the sensing region, and a second coil disposed on the substrate and coupled to the first coil. A method for operating the sensing system is also presented.

27 Claims, 9 Drawing Sheets

(56) References Cited

U.S. PATENT DOCUMENTS

| | | | |
|---|---|---|---|
| 8,779,768 B2* | 7/2014 | Brey | G01R 33/38 |
| | | | 324/307 |
| 9,880,117 B2* | 1/2018 | Fournier | G01N 27/00 |
| 9,903,850 B2* | 2/2018 | Harrison | G01N 33/2835 |
| 9,939,418 B2* | 4/2018 | Eriksson | G01N 33/2823 |
| 9,939,462 B2* | 4/2018 | Glocker | G01R 1/067 |
| 9,952,135 B2* | 4/2018 | Ayliffe | G01N 15/1404 |
| 9,952,192 B2* | 4/2018 | Donzier | G01N 33/28 |
| 2001/0015643 A1 | 8/2001 | Neil et al. | |
| 2002/0130661 A1* | 9/2002 | Raftery | G01R 33/307 |
| | | | 324/318 |
| 2007/0000321 A1 | 1/2007 | Boudaoud et al. | |
| 2010/0018305 A1 | 1/2010 | Maute et al. | |
| 2012/0116683 A1 | 5/2012 | Potyrailo et al. | |
| 2012/0161787 A1 | 6/2012 | Potyrailo et al. | |
| 2012/0235690 A1 | 9/2012 | Potyrailo et al. | |
| 2014/0002111 A1* | 1/2014 | Potyrailo | H05K 1/16 |
| | | | 324/655 |
| 2015/0115983 A1 | 4/2015 | Potyrailo et al. | |
| 2016/0018381 A1* | 1/2016 | Potyrailo | G01N 27/026 |
| | | | 324/633 |

OTHER PUBLICATIONS

Simonetta Capone et al. "Metal oxide gas sensor array for the detection of diesel fuel in engine oil", vol. 131, Issue 1, pp. 125-133, Apr. 14, 2008.

L. Guan et al. "Engine lubricating oil classification by SAE grade and source based on dielectric spectroscopy data", Analytica Chimica Acta, vol. 628, Issue 1, pp. 117-120, Oct. 17, 2008.

Jaedong Cho et al. "Capacitive sensor for automotive engine oil degradation using wireless network", Advanced Packaging Materials: Microtech, 2010. APM '10. International Symposium on, pp. 88-91, Feb. 28, 2010-Mar. 2, 2010, Cambridge.

Sedat Sen et al. "Evaluation of sensor arrays for engine oils using artificial oil alteration", Proc. SPIE 8066, Smart Sensors, Actuators, and MEMS V, 80662C, vol. 8066, May 5, 2011.

L. Guan et al. "Application of dielectric spectroscopy for engine lubricating oil degradation monitoring", vol. 168, Issue: 1, pp. 22-29, Jul. 2011.

Usman Latif et al. "Conductometric Sensors for Monitoring Degradation of Automotive Engine Oil", vol. 11(9), 8611-8625, Sep. 5, 2011.

Perez A.T et al. "Low-Cost Oil Quality Sensor Based on Changes in Complex Permittivity", 10675-10690, Nov. 10, 2011.

J.E. De Souzaa et al. "A close dielectric spectroscopic analysis of diesel/biodiesel blends and potential dielectric approaches for biodiesel content assessment", Fuel, vol. 105, pp. 705-710, Mar. 2013.

Idros M.F.M et al. "Condition based engine oil degradation monitoring system, synthesis and realization on ASIC", Aug. 27-29, 2014, pp. 84-87, Kuala Lumpur.

Junda Zhu et al. "Survey of Lubrication Oil Condition Monitoring, Diagnostics, and Prognostics Techniques and Systems", 2015.

\* cited by examiner

SENSING SYSTEM AND AN ASSOCIATED METHOD THEREOF

BACKGROUND

Embodiments of the present invention generally relate to an integrated sensor probe for monitoring of health of an industrial fluid and more specifically, to a sensor probe disposed in a housing with preserved sensor sensitivity and selectivity.

Real time monitoring of health of an industrial fluid, for example, engine oil is important in the field of transportation, such as, locomotive, marine, automotive, and the like. The real time monitoring of the health of the engine oil aids in providing early detection of leaks of diverse industrial fluids into engine oil and early detection of oil degradation and aging. Different types of sensors and sensing techniques have been designed to detect different aspects of oil health. Sensors include a mechanical resonator, an acoustic wave device, a capacitive sensor, a conductometric sensor, and sensor arrays. The different sensing techniques include dielectric spectroscopy and complex permittivity measurements.

However, the sensors and their electronic components currently employed for monitoring health of engine oil may be large in size. Therefore, these sensors are difficult or impossible to install in confined places in the engine. Hence, the sensor applicability may be adversely affected. In particular, the ability to install sensors in confined places in the engine is compromised.

Accordingly, there is a need for an enhanced system.

BRIEF DESCRIPTION

In accordance with one embodiment of the present invention, a sensing system for monitoring an industrial fluid is disclosed. The sensing system includes a housing and a sensor probe disposed at least partially in the housing. The sensor probe includes a substrate, a sensing region disposed on the substrate, a first coil disposed on the substrate and coupled to the sensing region, and a second coil disposed on the substrate and coupled to the first coil.

In accordance with another embodiment of the present invention, a method for operating a sensing system is disclosed. The method includes exciting a sensor probe in operational contact with an industrial fluid. The sensor probe is disposed at least partially in a housing. The sensor probe includes a substrate, a sensing region disposed on the substrate, a first coil disposed on the substrate and coupled to the sensing region, and a second coil disposed on the substrate and coupled to the first coil. The method also includes operating the sensor probe at one or more frequencies in a frequency range of analysis of the industrial fluid based on the excitation. Further, the method includes generating an output signal from the sensor probe across the frequency range of analysis of the industrial fluid and determining one or more properties of the industrial fluid based at least in part of the output signal generated from the sensor probe.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect. Furthermore, the terms "circuit", "circuitry", and "controller" may include either a single component or a plurality of components, which are either active and/or passive and are connected or otherwise coupled together to provide the described function. Also, the term "operatively coupled" as used herein includes wired coupling, wireless coupling, electrical coupling, magnetic coupling, radio communication, software based communication, or combinations thereof.

The term "fluids" can include liquids, gases, vapors, and solids and their combinations forming multiphase compositions. Non-limiting examples of multiphase compositions include emulsions such as oil/water emulsions, food emulsions such as salad dressings oil-in-water emulsions, colloids such as solutions that have particles distributed throughout the solution, food colloids, food colloids such as ice scream, jam, mayonnaise, solid foams such as bread, cake. Fluid can also include a food product that has been gone through mechanical re-forming. Alternatively, a fluid may not include a solid. Fluid can also include industrial, non-industrial, and/or naturally occurring fluids. Fluids may include naturally occurring fluids such as air, hydrocarbons, water, oils, body fluids, biological fluids, and the like that occur in natural living and non-living systems.

The term "industrial fluid" as used herein includes fluids that typically may be used on an industrial site or structure. In one example, the industrial fluid is at least one of a lubricant, a fuel, a hydraulic media, a drive fluid, a power steering fluid, a solvent, a power brake fluid, a drilling fluid, an oil, an insulating fluid, a heat transfer fluid, compressed air, ambient air, water, a naturally occurring fluid, or a synthetic fluid. In one example, the industrial fluid is a lubricating oil with known type and level of additives designed for exposure to multiple environmental conditions and with different wear protection and different particles-deposit control.

The term "multivariable sensor" as used herein refers to a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof. The multivariable sensor has a sensing region that is in operational contact with a fluid. The multivariable sensor may be in an operational contact with a fluid where the sensing region is bare or coated with a protective layer or with a sensing film.

The terms "transducer" and "sensor" as used herein refer to electronic devices such as LCR resonator intended for sensing. "Transducer" is a device before it is calibrated for a sensing application. "Sensor" is a device typically after it is calibrated for the sensing application. The sensor has a fluid-sensing region with an electrode. The fluid sensing region with the electrode may be alternatively referred to as a sensor probe. The sensing region may be placed in operational contact with a fluid of interest.

The electrical field may be applied by a sensor probe. The sensor probe may be in direct or indirect electrical contact with the industrial fluid. A sensing region may be either bare or coated with a protective dielectric layer or a sensing layer. In each of the disclosed cases, the sensing region may be considered to be in operational contact with a fluid. One example of indirect electrical contact with the fluid may be when a sensor probe is coated with a dielectric protective coating and when the electric field that may be generated by the sensor probe interacts with the fluid after penetrating through the dielectric protective coating. A suitable dielectric protective coating may be conformally applied to the sensor probe.

The sensor probe may be coated with a sensing material that is responsive to one or more fluid components of interest. When the sensor probe is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

The sensor probe may detect characteristics of the fluid via a resonant impedance spectral response. One or more of the LCR resonators may measure the resonant impedance spectral response. As opposed to simple impedance measurements, the disclosed embodiments probe the sample with at least one resonant electrical circuit. The resonant impedance spectrum of the sensor probe in proximity to the sample (the sensor in operational contact with the fluid) varies based on sample composition and/or components and/or temperature. The measured resonant impedance values $Z'$ (which may be the real part of resonant impedance, $Zre$) and $Z''$ (which may be the imaginary part of resonant impedance, $Zim$) reflect the response of the fluid (for example, the portion of the fluid in proximity to the sensor) to a stimulus of the electric field of a resonant electrical circuit.

As will be described in detail hereinafter, various embodiments of an exemplary sensing system for monitoring an industrial fluid are disclosed. Specifically, a sensing system includes a sensor probe disposed in a housing. The sensor probe disposed in the housing, has preserved sensor sensitivity and selectivity compared to a sensor probe disposed outside the housing. In other words, if the sensor probe is disposed in the housing, the sensor sensitivity and selectivity are not compromised. The specific design parameters of the housing and sensor probe packaging in the housing allows the sensor probe to provide sensitive, selective, and stable response. The housing wall thickness may be in the range from about 0.1 millimeter to about 10 millimeters.

Figure 1:
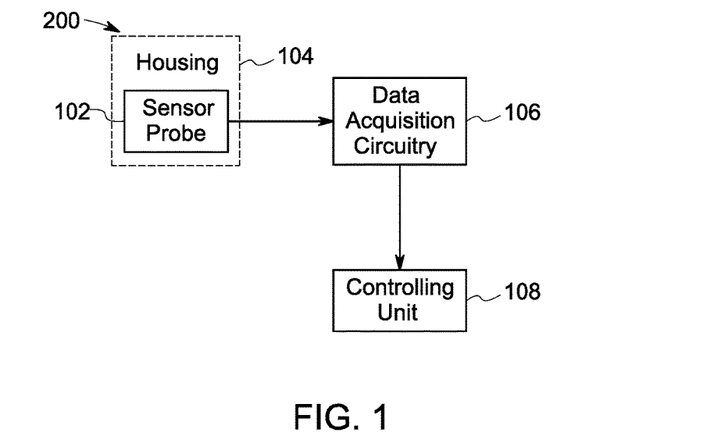
FIG. 1 is a block diagram of a sensing system in accordance with certain embodiments of the present invention.

Turning now to the drawings and by way of example in FIG. 1, a block diagram of a sensing system 100 in accordance with certain embodiments of the present invention is presented. The sensing system 100 includes a sensor probe 102, a housing 104, a data acquisition circuitry (DAC) 106, and a controlling unit 108. The sensor probe 102 is disposed at least partially in the housing 104. The sensor probe 102 includes a multivariable inductance-capacitance-resistance (LCR) resonator, in one non-limiting example.

In one embodiment, the housing 104 is configured to provide a radio frequency shielding for the sensor probe 102. In another embodiment, the housing 104 is also configured to withstand temperature of at least 250 degrees Celsius. In yet another embodiment, the housing 104 is configured to hermetically seal the sensor probe 102. The sensor probe 102 and the housing 104 together form a sensing unit 200.

In one embodiment, the sensor probe 102 is in operational contact with an industrial fluid. The sensor probe 102 may be configured to measure data such as a resonance impedance spectrum corresponding to the industrial fluid. In another embodiment, the data may be any parameter associated with properties such as complex permittivity of the industrial fluid.

Furthermore, the data may be acquired by the DAC 106. The DAC 106 is coupled to the controlling unit 108. The data acquired by the DAC 106 may be further processed by the controlling unit 108 to identify occurrence of any anomaly in the industrial fluid. In particular, composition/properties of the industrial fluid may be determined by processing of the data acquired in the DAC 106. In one embodiment, the level of water in the industrial fluid may be determined.

The controlling unit 108 includes one or more processors. The processor is configured to perform the functions of the controlling unit 108. As used herein, the term "processor" refers not only to integrated circuits included in a computer, but also refers to a controller, a microcontroller, a microcomputer, a programmable logic controller (PLC), an application specific integrated circuit, application-specific processors, digital signal processors (DSPs), Application Specific Integrated Circuits (ASICs), Field Programmable Gate Arrays (FPGAs), and/or any other programmable circuits.

Furthermore, the system 100 may include a memory device to store the data acquired using the sensor probe 102 or to store any data after being processed by the controlling unit 108. The memory device(s) may generally include memory element(s) including, but are not limited to, computer readable medium (e.g., random access memory (RAM)), computer readable non-volatile medium (e.g., a flash memory), one or more hard disk drives, a floppy disk, a compact disc-read only memory (CD-ROM), compact disk-read/write (CD-R/W) drives, a magneto-optical disk (MOD), a digital versatile disc (DVD), flash drives, optical drives, solid-state storage devices, and/or other suitable memory elements.

Figure 2:
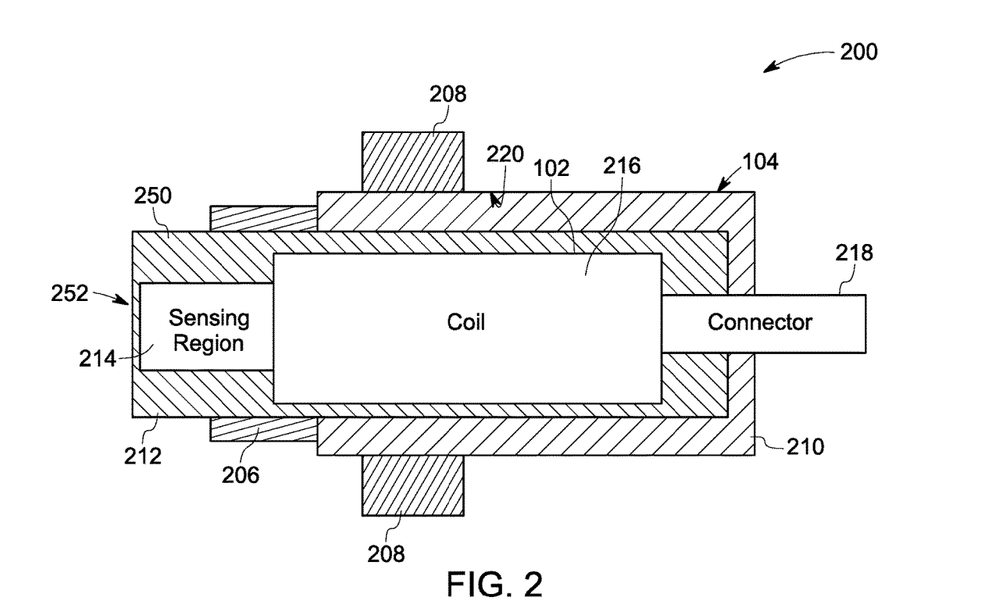
FIG. 2 is a diagrammatical representation of one embodiment of the sensing unit of FIG. 1.

Referring now to FIG. 2, a diagrammatical representation of one embodiment of the sensing unit 200 is presented. In the illustrated embodiment, a portion of the sensor probe 102 is disposed in the housing 104 is depicted.

The housing 104 includes a thread portion 206, a flange portion 208, and a body portion 210. In one embodiment, the housing 104 is a tubular structure, where either ends of the housing 104 are open. If the housing 104 is a tubular structure, then the thread portion 206, the flange portion 208, and the body portion 210 may have different diameters. In one specific embodiment, the flange portion 208 may have a larger diameter compared to the thread portion 206 and the body portion 210. In such an embodiment, the thread portion 206 has a smallest diameter. The housing 104 is made of at least one of metal, stainless steel, aluminum, metal alloys, metal-ceramic composites, and metal dielectric composites.

The sensor probe 102 includes a substrate 212, a sensing region 214, a coil 216, and a connector 218. The substrate 212 is made of at least one of a ceramic material, a composite material, an inorganic material, and a polymeric material.

Figure 3:
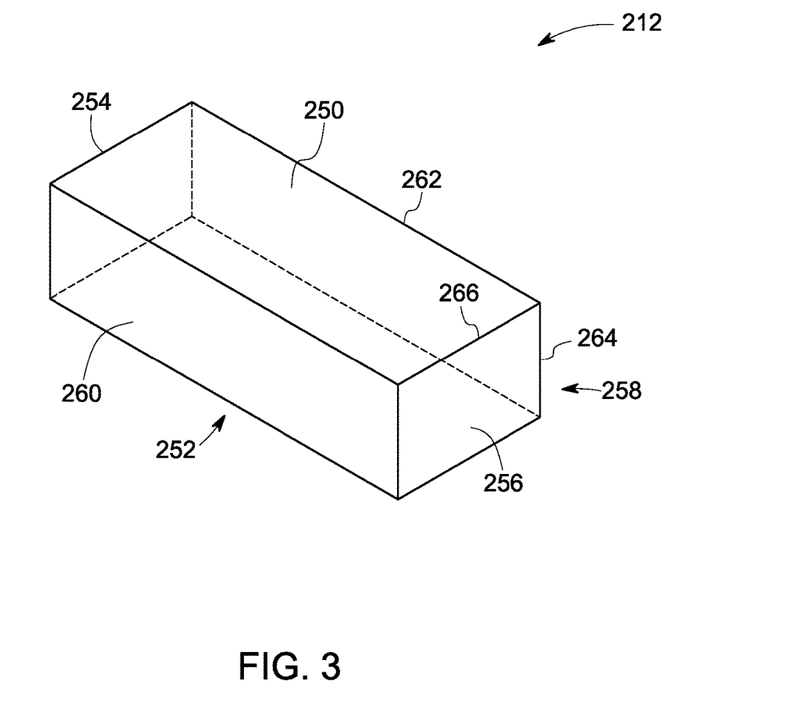
FIG. 3 is a perspective view of a substrate in accordance with the embodiment of FIG. 2.

Referring now to FIG. 3, a perspective view of the substrate 212 in accordance with an exemplary embodiment is presented. The substrate 212 has a shape of a rectangular cuboid. In particular, the substrate includes a first face 250, a second face 252 opposite to the first face 250, a third face 254 perpendicular to the first face 250 and the second face 252, a fourth face 256 opposite to the third face 254. Further, the substrate 212 includes a fifth face 258 perpendicular to the first face 250, the second face 252, the third face 254, and the fourth face 256, and a sixth face 260 opposite to the fifth face 258. Furthermore, the substrate 212 has a length 262, a depth 264, and a breadth 266. In one non-limiting embodiment, dimensions of the substrate 212 may range from about 0.1 mm×0.1 mm to about 100 mm×100 mm.

The substrate 212 may have different shapes such as a rectangular shape, a circular shape, and the like. In one embodiment, the area of the substrate 212 that is in operational contact with the industrial fluid may be in the range of about 0.01 mm² to about 1000 mm².

Referring back to FIG. 2 in combination with FIG. 3, only the first face 250 of the substrate 212 is depicted. The sensing region 214, the coil 216, and the connector 218 are disposed on the substrate 212. Specifically, the sensing region 214 and the coil 216 are disposed on the first face 250 of the substrate 212. The coil 216 is an inductor coil for the sensing region 214. The connector 218 is disposed on the second face 252 of the substrate 212.

Furthermore, the sensing region 214 is galvanically coupled to the coil 216. In particular, the sensing region 214 is directly coupled to the coil 216. In one embodiment, a combination of the coil 216 and the sensing region 214 forms an inductor-capacitor-resistor (LCR) resonator. In one embodiment, the sensing region 214 includes an interdigital electrode. Reference numeral 220 is representative of an inner surface of the housing 104. The sensor probe 102 is disposed at a predetermined distance apart from the inner surface 220 of the housing 104. In one non-limiting embodiment, the predetermined distances may range from about 1 mm to about 20 mm. Furthermore, the sensor probe is packaged to have minimal effects due to thermal shocks, mechanical shocks, and electrical shocks.

Further, the housing 104 is configured to direct flow of the industrial fluid to the sensing region 214 such that the sensing region 214 is in operational contact with the industrial fluid. In the illustrated embodiment, the substrate 212 and a portion of the sensing region 214 protrude outwards from the housing 104. In particular, the substrate 212 and the portion of the sensing region 214 extend outwards from the thread portion 206 of the housing 104. Further, the connector 218 extends outward from the housing 104. Specifically, the connector 218 extends outward from the body portion 210 of the housing 104.

In one embodiment, length of the housing 104 may be in a range from about 1 mm to about 100 mm. Further, cross-sectional area of the housing 104 may be in a range from about 1 mm² to about 1000 mm². The housing 104 may have different cross sections such as a rectangular cross section, a circular cross section, and the like.

Figure 4A:
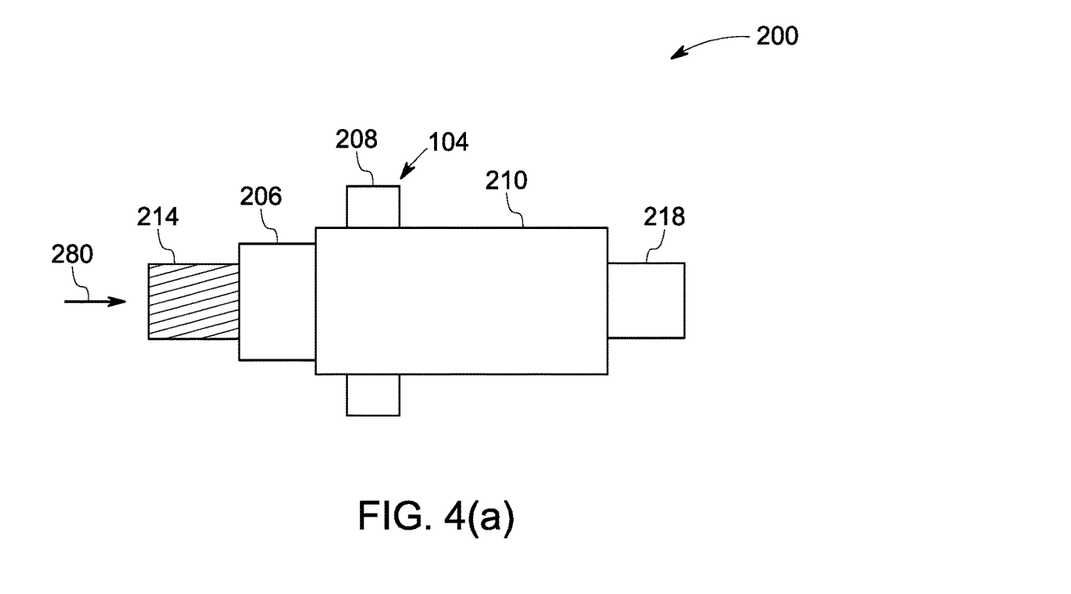
FIG. 4(a) is a top view of the sensing unit in accordance with the embodiment of FIG. 2.

FIG. 4(a) is a top view of the sensing unit 200 in accordance with one embodiment. The sensing region 214, the housing 104, and connector 218 are depicted. The housing 104 includes the thread portion 206, the flange portion 208, and the body portion 210. The sensing region 214 and the connector 218 extend outwards from either ends of the housing 104.

Figure 4B:
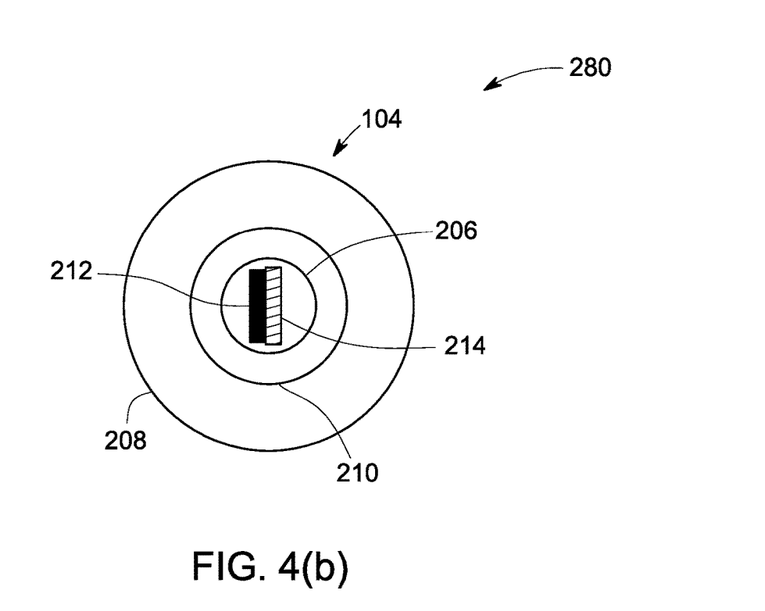
FIG. 4(b) is a side view of the sensing unit in accordance with the embodiment of FIG. 4(a)

FIG. 4(b) is a side view 280 of the sensing unit 200 of FIG. 5(a) in accordance with one embodiment. In the illustrated embodiment, a portion of the sensing unit 200 having the sensing region 214 and the housing 104, is presented. The sensing region 214 is disposed on the substrate 212. An outer periphery of the thread portion 206, the flange portion 208, and the body portion 210 are shown.

Figure 5:
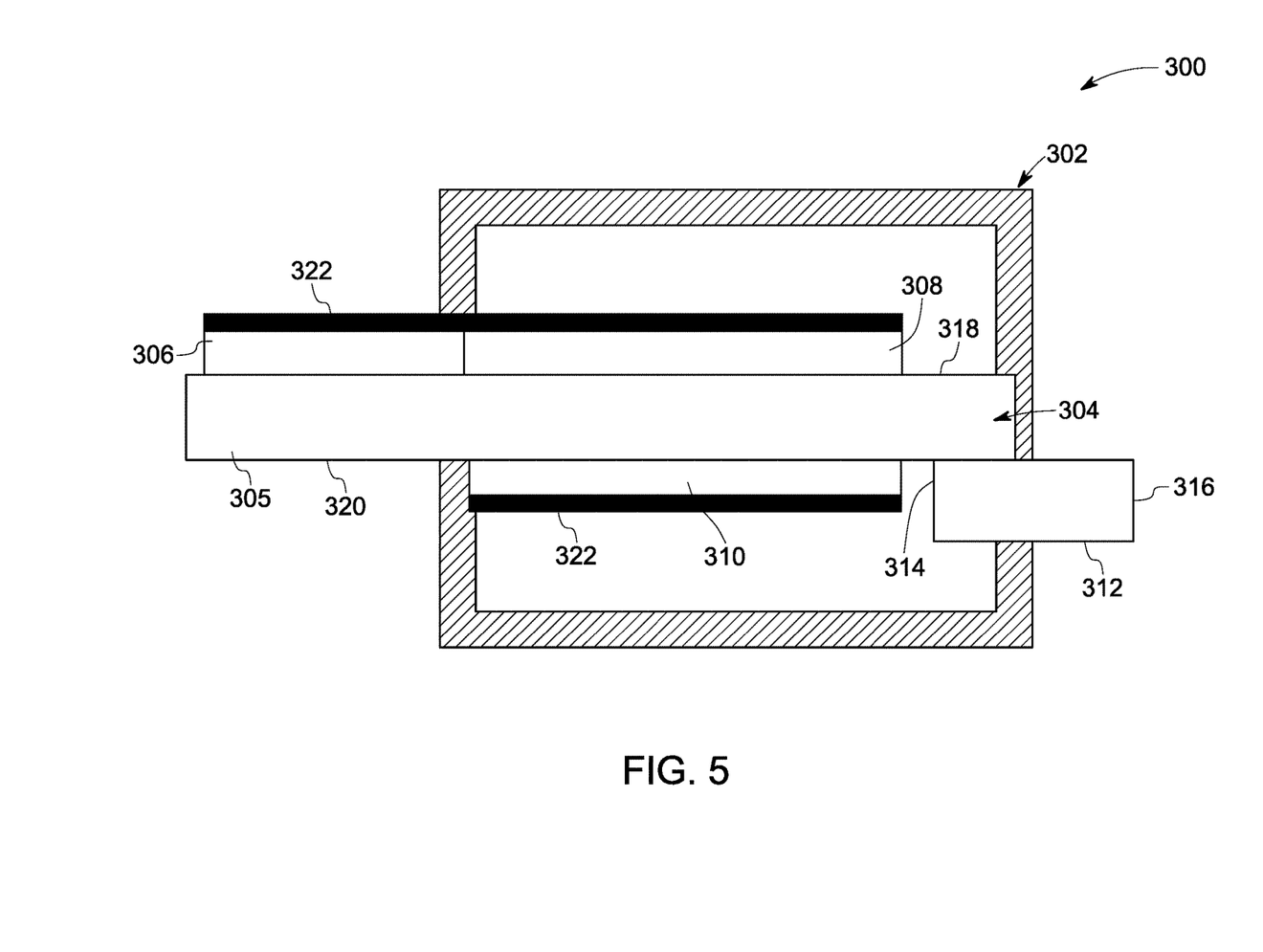
FIG. 5 is a diagrammatical representation of a sensing unit in accordance with another exemplary embodiment.

FIG. 5 is a diagrammatical representation of a sensing unit 300 in accordance with another exemplary embodiment. The sensing unit 300 includes a housing 302 and a sensor probe 304. The sensor probe 304 is disposed at least partially in the housing 302. The sensor probe 304 includes a substrate 305, a sensing region 306, a first coil 308, a second coil 310, and a connector 312. The sensing region 306 and the first coil 308 are disposed on a first face 318 (similar to the first face 250 of FIG. 3) of the substrate 305. The second coil 310 and the connector 312 are disposed on a second face 320 (similar to the second face 252 of FIG. 3) of the substrate 305.

The first coil 308 and the sensing region 306 are galvanically coupled to each other. Further, the second coil 310 is inductively coupled to the first coil 308 and the sensing region 306. The sensor probe 304 is configured to provide an impedance match between the first coil 308 and the second coil 310. In one embodiment, the second coil 310 is an inductive pick up coil. Furthermore, the second coil 310 is non-galvanically coupled to the first coil 308 and the sensing region 306. The second coil 310 is configured to acquire a response from the first coil 308 and the sensing region 306. In one embodiment, the response from the first coil 308 and the sensing region 306 may be similar. In another embodiment, the response from the first coil 308 and the sensing region 306 may be different. In one specific embodiment, the response from the first coil 308 may be a function of the response from the sensing region 306.

The connector 312 is galvanically coupled to the second coil 310. The connector 312 has a first end 314 and a second end 316. The first end 314 of the connector 312 is coupled to the second coil 310. Further, the second end 316 of the connector 312 is configured to deliver an output signal of the sensor probe 304. The output signal of the sensor probe 304 is provided to the data acquisition circuitry such as the DAC 106 of FIG. 1. The sensor probe 304 further includes a dielectric material layer 322 disposed on at least one of the sensing region 306, the first coil 308, and the second coil 310. Furthermore, the housing 302 is configured to provide an environmental sealing for the first coil 308 and the second coil 310.

Figure 6A:
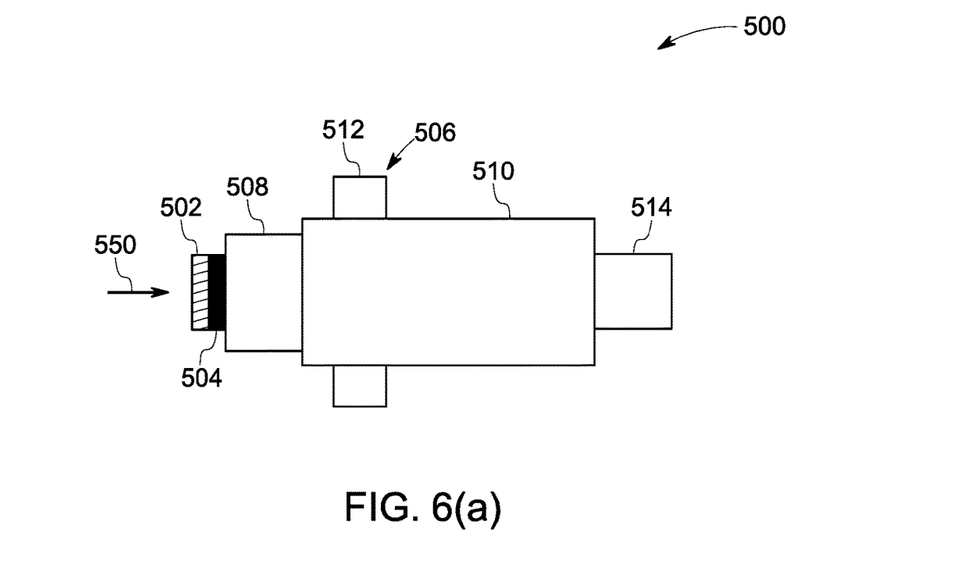
FIG. 6(a) is a top view of another embodiment of a sensing unit in accordance with another embodiment.

FIG. 6(a) is a diagrammatical representation of a top view of another embodiment of a sensing unit 500. In the illustrated embodiment, a portion of the sensing unit 500 includes a sensing region 502, a substrate 504, a housing 506, and a connector 514 is depicted. The sensing region 502 is disposed on the substrate 504. In particular, the sensing region 502 is disposed on a face (similar to the third face 254 of FIG. 3) of the substrate 504. The housing 506 includes a thread portion 508, a flange portion 512, and a body portion 510.

Figure 6B:
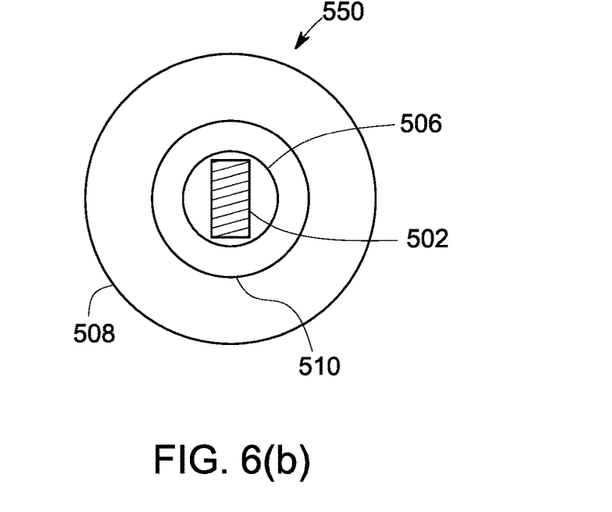
FIG. 6(b) is a side view of the sensing unit in accordance with the embodiment of FIG. 6(a)

FIG. 6(b) is a diagrammatical representation of a side view 550 of the sensing unit 500 of FIG. 6(a). In the illustrated embodiment, a portion of the sensing unit 500 having the sensing region 502 and the housing 506 is shown. The housing 506 includes the thread portion 508, the flange portion 512, and the body portion 510. An outer periphery of the thread portion 508, the flange portion 512, and the body portion 510 are shown.

Figure 7A:
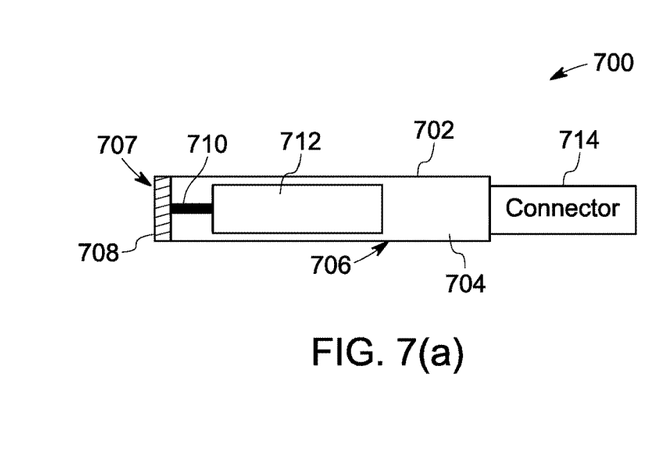
FIG. 7(a) is a top view of a sensor probe in accordance with another embodiment.

FIG. 7(a) depicts a top view of a sensor probe 700 in accordance with another embodiment. In particular, only a portion of the sensor probe 700 is depicted. The sensor probe 700 includes a substrate 702, a sensing region 708, a coil 712, and a connector 714.

The coil 712 is disposed on a first face 704 (similar to first face 250 of FIG. 3) of the substrate 702. The connector 714 is disposed on the second face 706 (similar to the second face 252 of FIG. 3) of the substrate 702. The connector 714 extends outward from the substrate 702. The sensing region 708 is disposed on a third face 707 (similar to the third face 254 of FIG. 3) of the substrate 702. Further, the coil 712 is galvanically coupled to the sensing region 708 via a coupling 710.

Figure 7B:
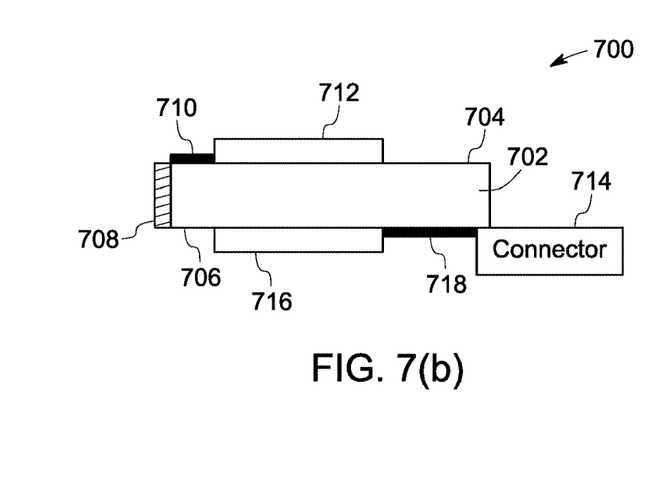
FIG. 7(b) is a side view of a sensor probe of FIG. 7(a) in accordance with another exemplary embodiment.

Referring now to FIG. 7(b), a side view of a sensor probe 700 of FIG. 7(a) is presented. The sensor probe 700 includes a substrate 702, a sensing region 708, a first coil 712, a second coil 716, and a connector 714.

The first coil 712 disposed on the first face 704 (similar to first face 250 of FIG. 3) of the substrate 702. The second coil 716 is disposed on a second face 706 (similar to the second face 252 of FIG. 3) of the substrate 702. The second coil 716 is inductively coupled to the first coil 712. The second coil 716 may also be referred to as an inductive pick up coil. The second coil 716 is configured to pick up signals from the first coil 712. The second coil 716 is further galvanically coupled to one end of the connector 714 via a coupling 718. The output signal is obtained at the other end of the connector 714. The sensing region 708 is disposed on a third face 707 (similar to the third face 254 of FIG. 3) of the substrate 702. Further, the sensing region 708 is galvanically coupled to the first coil 712 via the coupling 710. The first coil 712 is configured to pick up the signals sensed by the sensing region 708. The signals sensed by the sensing region 708 are transmitted as an output signal via the first coil 712, the second coil 716, and the connector 714. The connector 714 extends outward from the substrate 702.

Figure 7C:
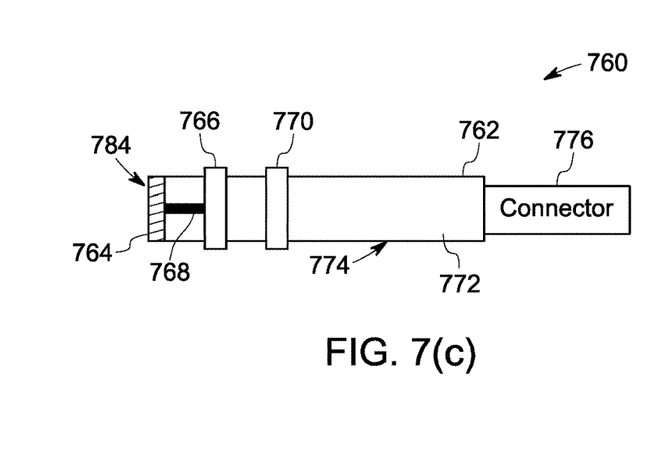
FIG. 7(c) is a top view of a sensor probe in accordance with another exemplary embodiment.

Referring to FIG. 7(c), a top view of a sensor probe 760 in accordance with another embodiment is presented. In the illustrated embodiment, a portion of the sensor probe 760 is shown. The sensor probe 760 includes a substrate 762, a sensing region 764, a first coil 766, a second coil 770, and a connector 776.

The first coil 766 and the second coil 770 extend coaxially along the substrate 762. In one embodiment, the first and second coils 766, 770 are ring-like structures. Further, the first coil 766 is disposed at a predetermined distance apart from the second coil 770. In one non-limiting embodiment, the predetermined distance may be in a range from about 0.1 mm to about 10 mm.

The connector 776 is disposed on a second face 774 (similar to the second face 252 of FIG. 3) of the substrate 762. Further, the connector 776 extends outward from the substrate 762. The sensing region 764 is disposed on a third face 784 (similar to the third face 254 of FIG. 3) of the substrate 762. The sensing region 764 is galvanically coupled to the first coil 766 via a coupling 768.

Figure 7D:
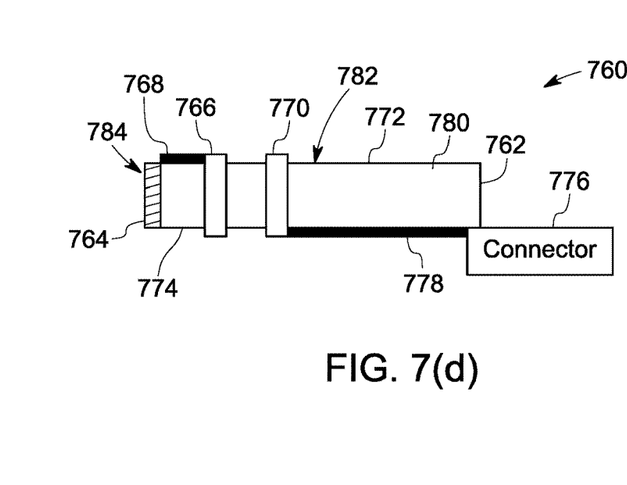
FIG. 7(d) is a side view of a sensor probe of FIG. 7(c) in accordance with another exemplary embodiment.

Referring now to FIG. 7(d), a side view of a sensor probe 760 of FIG. 7(c) is presented. The sensor probe 760 includes a substrate 762, a sensing region 764, a first coil 766, a second coil 770, and a connector 776.

The sensing region 764, the first coil 766, and the second coil 770 are disposed on the substrate 762. The first coil 766 and the second coil 770 extend coaxially along the substrate 762. In particular, the first coil 766 and the second coil 770 are disposed partially on a portion of faces 772, 774, 780, and 782. The face 772 is a first face (similar to the first face 250 of FIG. 3), the face 774 is the second face (similar to the second face 252 of FIG. 3), the face 780 is the fifth face (similar to the fifth face 258 of FIG. 3), and the face 782 is a sixth face (similar to the sixth face 260 of FIG. 3) of the substrate 762. The first coil 766 and the second coil 770 are coupled inductively. The sensing region 764 is galvanically coupled to the first coil 766 via the coupling 768. Further, the second coil 770 is galvanically coupled to the connector 776 via the coupling 778. The connector 776 is disposed on the substrate 762 and extends outward from the substrate 762.

Figure 8:
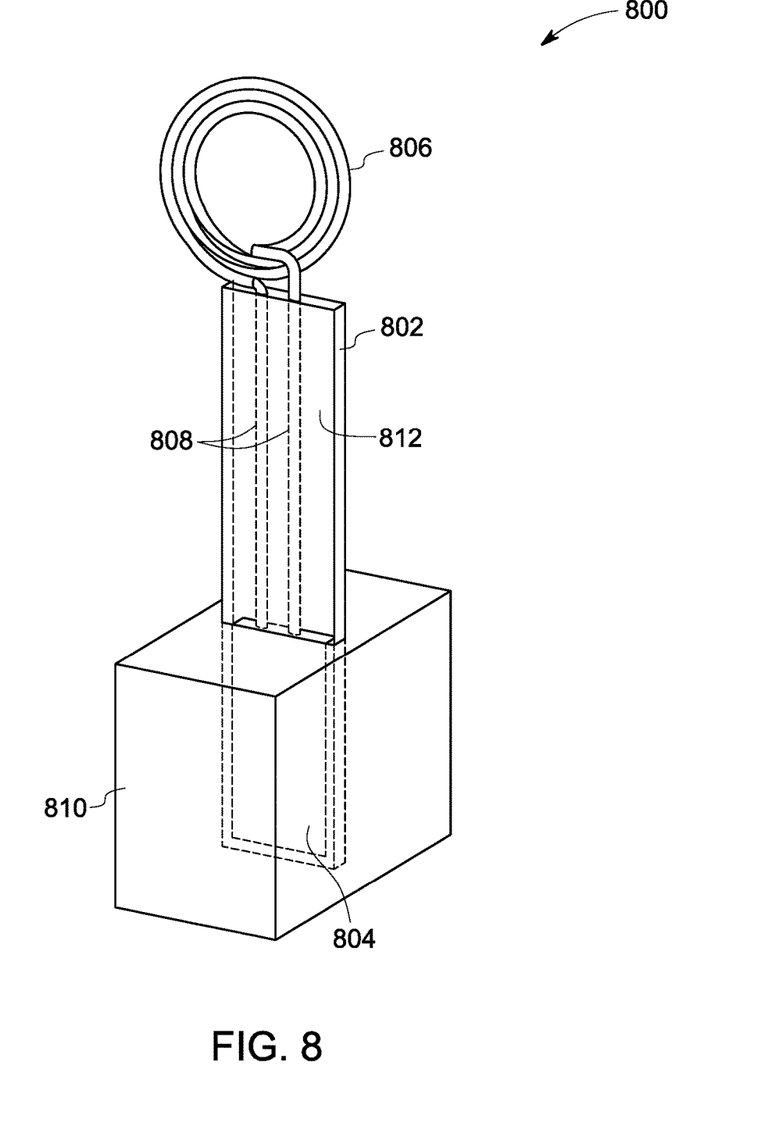
FIG. 8 is a diagrammatical representation of a sensor probe in accordance with the embodiment of FIG. 7(a)

FIG. 8 is a diagrammatical representation of one embodiment of a sensor probe 800 of FIG. 1. The sensor probe 800 includes a substrate 802. In one embodiment, the substrate 802 is a dielectric substrate. A sensing region 804 is disposed on the face 812 (similar to the first face 250 of FIG. 3) of the substrate 802. The sensing region 804 includes an interdigital electrode. Further, a coil 806 is coupled to the sensing region 804 via a coupling 808. The coil 806 extends outward from the substrate 802. Furthermore, the coupling 808 is disposed along the substrate 802. In the illustrated embodiment, the sensing region 804 is disposed in operational contact with industrial fluids 810. The properties of the industrial fluids 810 may be determined using the sensor probe 800.

Figure 9:
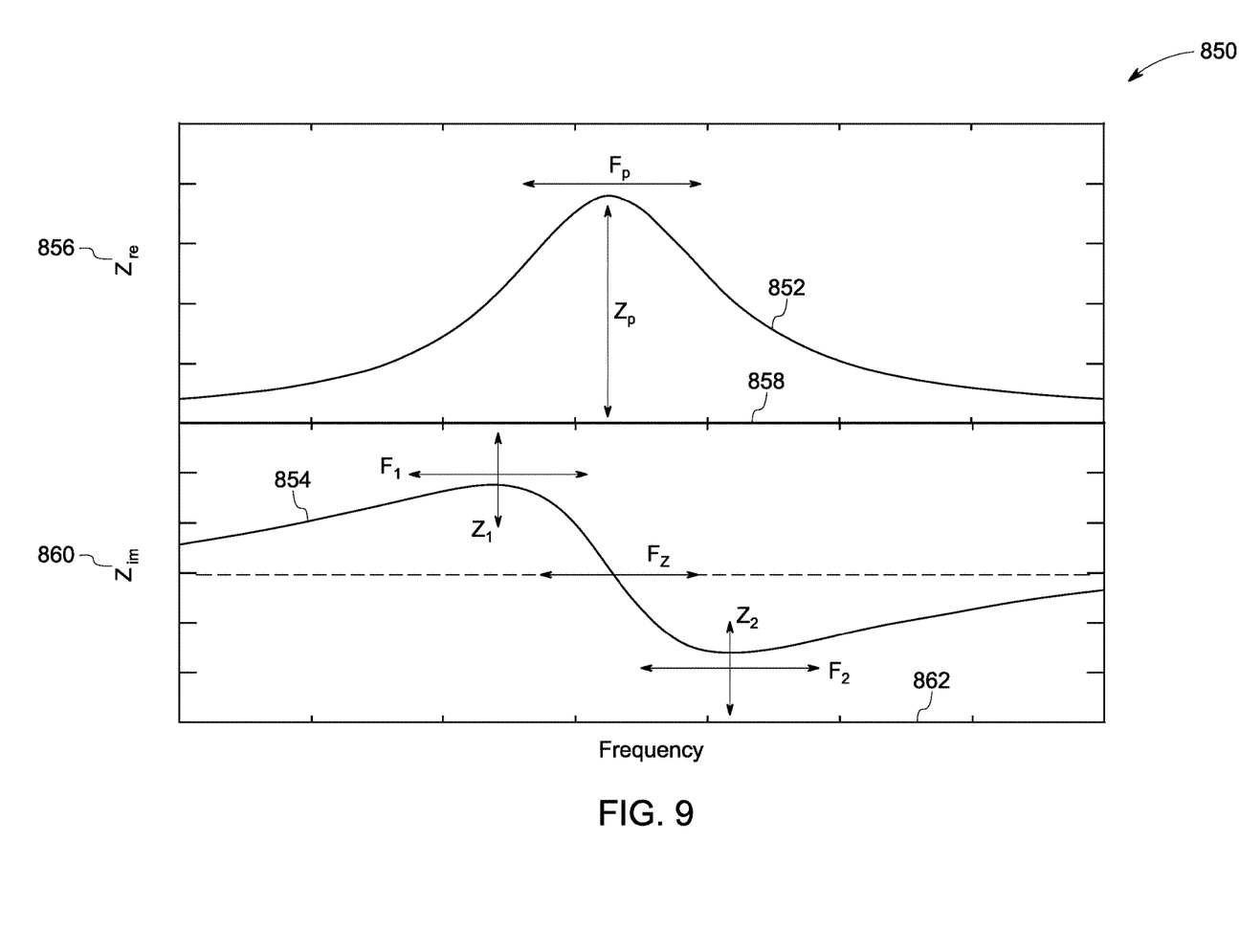
FIG. 9 is a diagrammatical representation of a resonance impedance spectrum of a sensor probe in accordance with the embodiment of FIG. 1.

FIG. 9 is a diagrammatical representation of a resonance impedance spectrum 850 of a sensor probe in accordance with the embodiment of FIG. 1. In particular, FIG. 9 represents a resonance impedance spectrum 850 of a LCR resonator. In one embodiment, the resonance impedance spectrum 850 is measured using an inductive coupling or a direct connection to a sensor reader. The resonance impedance spectrum (f) may be represented as:

(f)=$Z_{re}$(f)+j$Z_{im}$(f), where $Z_{re}$(f) is a real impedance spectrum and j$Z_{im}$(f) is an imaginary impedance spectrum.

In the illustrated embodiment, reference numeral 852 represents a real impedance spectrum $Z_{re}$(f) and reference numeral 854 represents an imaginary impedance spectrum $Z_{im}$(f). Further, reference numerals 856 and 860 represent the real impedance and imaginary impedance in ohms respectively. Further, reference numerals 858 and 862 represent frequency in hertz. The parameters that may be determined using the (f) resonance impedance spectrum include frequency position $F_p$ and magnitude $Z_p$ of $Z_{re}$(f) corresponding to frequency position $F_p$. Further, other parameters include a resonant frequency $F_1$ and an anti-resonant frequency $F_2$ and the impedance magnitudes $Z_1$ and $Z_2$ of imaginary impedance spectrum $Z_{im}$(f) corresponding to frequencies $F_1$ and $F_2$. Also, yet another parameter that may be determined using the resonance impedance spectrum includes a zero-reactance frequency $F_Z$ of imaginary impedance spectrum $Z_{im}$(f). In one embodiment, any variation in any of the abovementioned parameters of the resonance impedance spectrum may provide information regarding composition of an industrial fluid.

Figure 10:
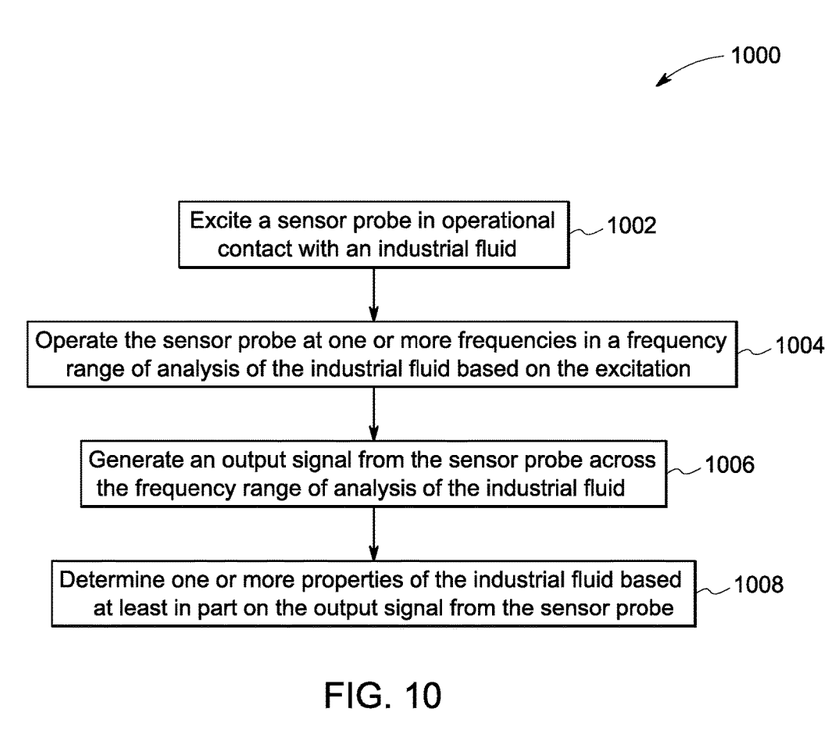
FIG. 10 is a flow chart representative of a method of operation of a sensing system in accordance with certain embodiments of the present invention.

Referring now to FIG. 10, a flow chart representative of a method for operating a sensing system in accordance with certain aspects of the present invention is presented. At block 1002, a sensor probe which is in operational contact with industrial fluid, is excited. The excitation of the sensor probe results in generation of an electrical field using the sensor probe. The electrical field is transmitted from the sensor probe to the industrial fluid.

Further, at block 1004, the sensor probe is operated at one or more frequencies in a frequency range of analysis of the industrial fluid based on the excitation. The sensor probe is a LCR resonator, where the LCR resonator is configured to operate at one or more frequencies in a frequency range of analysis.

At block 1006, an output signal from the sensor probe across the frequency range of analysis of the industrial fluid is generated. The output signal may be obtained at one end of a connector of the sensor probe. The output signal is representative of information about the industrial fluid. In one embodiment, the output signal is representative of a resonant impedance spectrum of the industrial fluid over a frequency range of analysis.

Furthermore, at block 1008, one or more properties of the industrial fluid based at least in part on the output signal from the sensor probe are determined. In one embodiment, one or more properties of the industrial fluid may be determined based at least in part on the resonant impedance spectrum. In one embodiment, the sensor probe may determine a complex permittivity of the industrial fluid. In particular, the complex permittivity of the industrial fluid may be determined based on the resonance impedance spectrum. In another embodiment, the complex permittivity of the industrial fluid may be representative of a measure of level of water in oil. The use of housing for packaging a sensor probe does not influence the sensitivity of the sensor probe.

Furthermore, the foregoing embodiments, and process steps may be implemented by suitable codes on a processor-based system, such as a general-purpose or special-purpose computer. It should also be noted that different implementations of the present technique may perform some or all of the steps described herein in different orders or substantially concurrently. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

In accordance with the exemplary embodiments discussed herein, the sensing system includes a housing at least partially enclosing the sensor probe. The housing aids in providing environmental sealing for the sensor probe, to withstand high temperature and provide RF shielding for the sensor probe. Furthermore, the housing is configured to protect the sensor probe from any damage. Moreover, in such embodiments, the sensor sensitivity and selectivity are not compromised. The specific design parameters of the housing and sensor probe packaging in the housing allows the sensor probe to provide sensitive, selective, and stable response. The non-limiting exemplary sensing system may be used in applications such as transportation, for example, locomotive, marine, automotive, and the like.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

The invention claimed is:

1. A sensing system for monitoring an industrial fluid, the sensing system comprising:
   a housing; and
   a sensor probe disposed at least partially in the housing, wherein the sensor probe is a resonant electrical circuit comprising:
   a substrate;
   a bare sensing region disposed on the substrate;
   a first coil disposed on the substrate and coupled to the bare sensing region; and
   a second coil disposed on the substrate and inductively coupled to the first coil,
   wherein the sensor probe is configured to generate an electric field which interacts with the industrial fluid.

2. The sensing system of claim 1, wherein the substrate comprises:
   a first face;
   a second face opposite to the first face;
   a third face perpendicular to the first face and the second face; and
   a fourth face opposite to the third face.

3. The sensing system of claim 2, wherein at least one of the bare sensing region and the first coil are disposed on the first face.

4. The sensing system of claim 2, wherein the second coil is disposed on the second face.

5. The sensing system of claim 2, wherein the bare sensing region is disposed on at least one of the third face and the fourth face.

6. The sensing system of claim 1, wherein the first coil and the second coil extend coaxially along the substrate, wherein the first coil is disposed at a predetermined distance apart from the second coil.

7. The sensing system of claim 1, wherein a combination of the first coil and the bare sensing region forms an inductor-capacitor-resistor (LCR) resonator.

8. The sensing system of claim 1, wherein the second coil is further coupled to the bare sensing region and is configured to acquire a response from the first coil and the bare sensing region.

9. The sensing system of claim 1, wherein the sensor probe further comprises a dielectric material layer disposed on at least one of the bare sensing region, the first coil, and the second coil.

10. The sensing system of claim 1, wherein the bare sensing region comprises an interdigital electrode.

11. The sensing system of claim 1, wherein the substrate comprises at least one of a ceramic material, a composite material, an inorganic material, and a polymeric material.

12. The sensing system of claim 1, wherein the housing comprises at least one of metal, stainless steel, aluminum, metal alloys, metal-ceramic composites, and metal dielectric composites.

13. The sensing system of claim 1, wherein the housing is configured to provide a radio frequency shielding for the sensor probe.

14. The sensing system of claim 1, wherein the housing is configured to provide an environmental sealing for the first coil and the second coil.

15. The sensing system of claim 1, wherein the housing is a tubular structure.

16. The sensing system of claim 1, wherein the housing is configured to direct a flow of the industrial fluid to the bare sensing region such that the bare sensing region is in operational contact with the industrial fluid.

17. The sensing system of claim 1, wherein the housing is configured to withstand a temperature of at least 250° C.

18. The sensing system of claim 1, wherein the sensor probe is disposed at a predetermined distance apart from an inner surface of the housing.

19. The sensing system of claim 1, wherein the housing hermetically seals the sensor probe.

20. The sensing system of claim 1, wherein the sensor probe further comprises a connector having a first end and a second end, wherein the first end is coupled to the second coil and the second end is configured to deliver an output signal of the sensor probe.

21. The sensing system of claim 20, further comprising at least one of a controlling unit and a data acquisition circuitry operatively coupled to the connector.

22. The sensing system of claim 21, wherein the data acquisition circuitry is configured to receive the output signal.

23. The sensing system of claim 1, wherein the sensor probe is configured to provide an inductive coupling between the bare sensing region and the second coil.

24. The sensing system of claim 1, wherein the sensor probe is configured to provide a non-galvanic coupling between the bare sensing region and the second coil.

25. The sensing system of claim 1, wherein the sensor probe is configured to provide an impedance match between the first coil and the second coil.

26. A method for operating a sensing system, the method comprising:
   exciting a sensor probe in operational contact with an industrial fluid, wherein the sensor probe is disposed at least partially in a housing, wherein the sensor probe is a resonant electrical circuit comprising a substrate, a bare sensing region disposed on the substrate, a first coil disposed on the substrate and coupled to the bare sensing region, and a second coil disposed on the substrate and inductively coupled to the first coil, and wherein the sensor probe is configured to generate an electric field which interacts with the industrial fluid;
   operating the sensor probe at one or more frequencies in a frequency range of analysis of the industrial fluid based on the excitation;
   generating an output signal from the sensor probe across the frequency range of analysis of the industrial fluid; and
   determining one or more properties of the industrial fluid based at least in part of the output signal generated from the sensor probe.

27. The method of claim 26, wherein the output signal generated from the sensor probe comprises a resonant impedance spectrum of the industrial fluid.

* * * * *